United States Patent [19]
Schläpfer et al.

[11] Patent Number: 5,993,449
[45] Date of Patent: Nov. 30, 1999

[54] BONE-FIXING DEVICE

[75] Inventors: Fridolin Schläpfer, Glarus; Alexander Hatebur, Basel, both of Switzerland

[73] Assignee: Synthes (USA), Paoli, Pa.

[21] Appl. No.: 09/077,366

[22] PCT Filed: Nov. 30, 1995

[86] PCT No.: PCT/CH95/00281

§ 371 Date: May 28, 1998

§ 102(e) Date: May 28, 1998

[87] PCT Pub. No.: WO97/19646

PCT Pub. Date: Jun. 5, 1997

[51] Int. Cl.[6] .................................................. A61B 17/56
[52] U.S. Cl. ................................................ 606/60; 606/70
[58] Field of Search .................... 606/69, 70, 71, 606/61, 60, 73; 623/17

[56] References Cited

U.S. PATENT DOCUMENTS

| | | |
|---|---|---|
| 4,289,123 | 9/1981 | Dunn . |
| 5,324,290 | 6/1994 | Zdeblick et al. . |
| 5,702,395 | 12/1997 | Hopf . |
| 5,713,898 | 2/1998 | Stücker et al. . |

*Primary Examiner*—Michael Buiz
*Assistant Examiner*—Jonathan D. Goldberg
*Attorney, Agent, or Firm*—Pennie & Edmonds LLP

[57] ABSTRACT

A device for the fixation of bones is disclosed. The device includes a block, a bone plate integral to the block which has at least one plate hole for accommodating a fastener, a first guide channel on the block for accommodating a first longitudinal carrier, and a second guide channel on the block for accommodating a second longitudinal carrier. The first and second guide channels are parallel to each other and the axes of the guide channels are in a plane which is parallel to the bone-contact surface of the bone plate. A cylinder defined by the first guide channel does not intersect the cylinders defined by the bone plate holes and a cylinder defined by the second guide channel does intersect the cylinders defined by the bone plate holes.

20 Claims, 4 Drawing Sheets

BONE-FIXING DEVICE

FIELD OF THE INVENTION

The invention relates to a device for the fixation of bones.

BACKGROUND

For the anterior fusion of vertebra segments (fractures, tumors, infections, congenital and post traumatic kyphoses, deformities) a wide variety of plate- as well as rod-systems are available.

Some of the advantages of plate systems such as the one disclosed in PCT/US93/08433, are the relatively small dimensions and the generally easy handling. Important disadvantages of these known plate-system consist therein that the area of fusion cannot actively be set under compression, a great assortment of expensive plate implants, and in the case of deformities no possibilities of correction.

Rod systems, such as the ones disclosed in PCT/US93/10908 or PCT/EP94/01606, do not have the above mentioned disadvantages of the plate-systems, but they are naturally larger in their dimensions and more difficult to handle.

U.S. Pat. No. 4,289,123 discloses an orthopedic appliance which includes a pair of brackets anchored to bone and connected by a pair of rods. However, the disclosed device is bulky and cumbersome to use.

SUMMARY OF THE INVENTION

The present invention provides a device which combines the advantages of the known plate- and rod-systems easy handling, platelike dimensions, an assortment favourable in costs as well as possibilities of compression and correction.

The device according to the present invention comprises a block, a bone plate associated with the block and having a bone-contact surface and at least one plate hole, and first and second parallel guide channels associated with the block for accommodating first and second longitudinal carriers. Each of the guide channels has a longitudinal axis lying in a plane which is parallel to the bone-contact surface and an imaginary cylinder defined by the first guide channel does not intersect an imaginary cylinder defined by the bone plate hole while an imaginary cylinder defined by the second guide channel intersects the imaginary cylinder defined by the bone plate hole.

The first guide channel extends completely through the block while the second guide channel extends partially through the block to form an opening in the block opposite the bone plate. At least one of the guide channels can extend to the side of the block opposite the bone-contact surface to facilitate insertion of a longitudinal carrier. Alternatively, at least one of the guide channels can extend to the top of the block to facilitate insertion of a longitudinal carrier.

The bone plate comprises at least two plate holes having centers which lie on a common connecting line. In one preferred embodiment, the connecting line is disposed at an angle of +10° to +50° with respect to the longitudinal axes of the first and second guide channels. In another preferred embodiment, the connecting line is disposed at an angle of −10° to −50° with respect to the longitudinal axes of the first and second guide channels.

Each guide channel includes a bore hole positioned orthogonal to its longitudinal axis to accommodate a fastener for removably securing a longitudinal carrier to the guide channel. The bone-contact surface includes a cylindrical segment having a cylinder radius of between 25 and 35 mm and a longitudinal axis which is parallel to the longitudinal axes of the first and second guide channels. Preferably, the plate holes have longitudinal axes lying in parallel planes which are perpendicular to the longitudinal axis of the cylindrical segment of the bone-contact surface.

The bone plate holes have a multiple-threaded threads preferably having a planar thread bottom. In a further preferred embodiment, the planar thread bottom forms an angle of between 20° and 40° with respect to the thread longitudinal axis. The plate holes can be spherical.

An apparatus for the fixation of bones according to the present invention includes first and second devices each comprising: a block; a bone plate associated with the block and having a bone-contact surface and at least one plate hole; and first and second parallel guide channels associated with the block for accommodating first and second longitudinal carriers, and each having a longitudinal axis lying in a plane which is parallel to the bone-contact surface so that an imaginary cylinder defined by the first guide channel does not intersect an imaginary cylinder defined by the bone plate hole while an imaginary cylinder defined by the second guide channel intersects the imaginary cylinder defined by the bone plate hole. The apparatus also includes first and second longitudinal carriers positioned in the first and second guide channels of the first and second devices.

Each guide channel includes a bore hole positioned orthogonal to its longitudinal axis to accommodate a fastener for removably securing the longitudinal carrier therein. Each bone plate comprises at least two plate holes having centers which lie on a common connecting line. At least one guide channel of each of the first and second devices can extend to the side of the block opposite the bone-contact surface to facilitate insertion of the longitudinal carrier. Alternatively, at least one guide channel of each of the first and second devices extends to the top of the block to facilitate insertion of the longitudinal carrier.

In use two complementarily shaped devices according to the invention are attached to two parallel longitudinal carriers. Each device is connected to the respective vertebral body by means of two bone screws. The bone screws have both a bone- and a machine thread. The two threads are arranged so that they provide the same pitch and pass over to one another seamlessly. The plate holes within the two devices provide the same machine thread as the bone screws. The geometry of the thread in the bone plate part of the device is shaped so that after fastening the screws the device and the screws are connected to each other at a stable angle and safe against vibrations.

The longitudinal carriers are directly connected to the two devices according to the invention and not to the bone screws. Thereto the block parts of the device according to the invention purposefully provide each a pocket hole and a through hole, wherein the longitudinal carriers can be inserted and fastened by means of adjusting screws. The holes for the longitudinal carriers are arranged such that the pocket hole on the block part on the one device aligns with the through hole of the other device and the bone screws can still be inserted also after the mounting of the longitudinal carriers. This particular arrangement and embodiment of the holes for the longitudinal carriers lead to all the above mentioned advantages of the combination according to the invention as easy handling, small dimensions and unlimited distraction/compression in situ.

The invention and further embodiments of the invention are discussed in more detail in the following section by means of the partial schematic representations of several embodiments.

DETAILED DESCRIPTION OF THE PREFERRED EMBODIMENT

Figure 1:
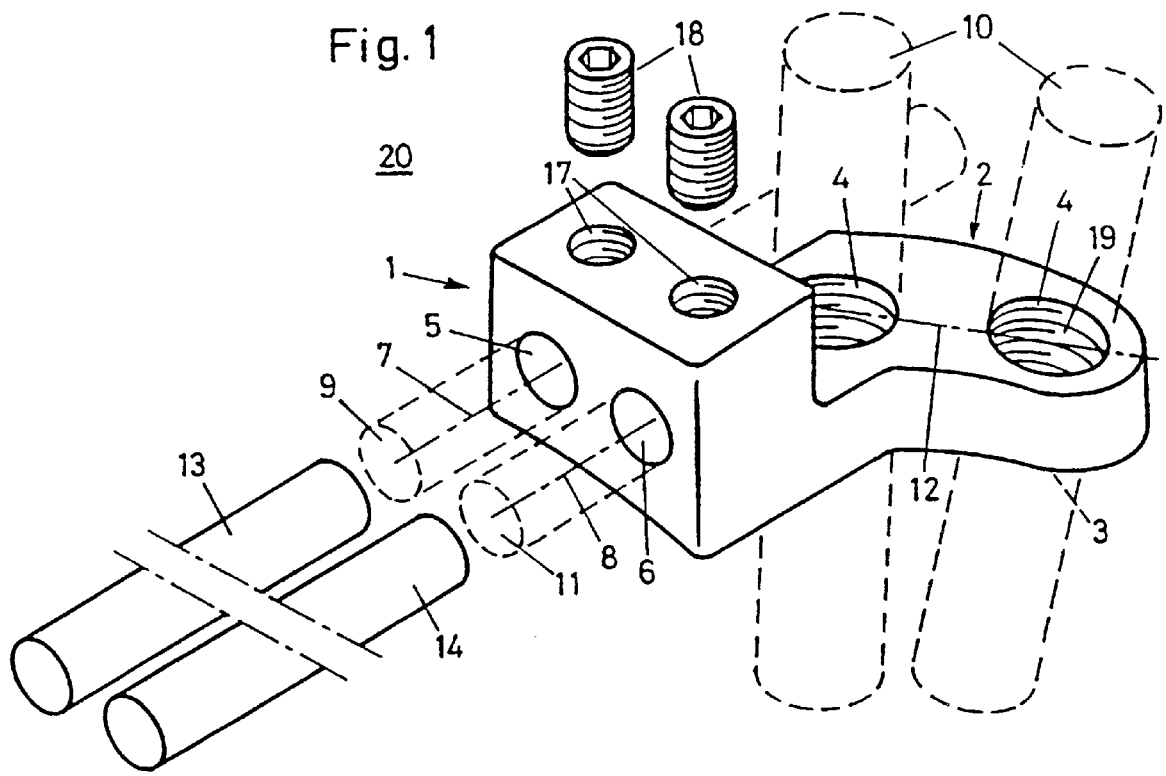
FIG. 1 a perspective representation of a first device according to the invention.
Figure 3:
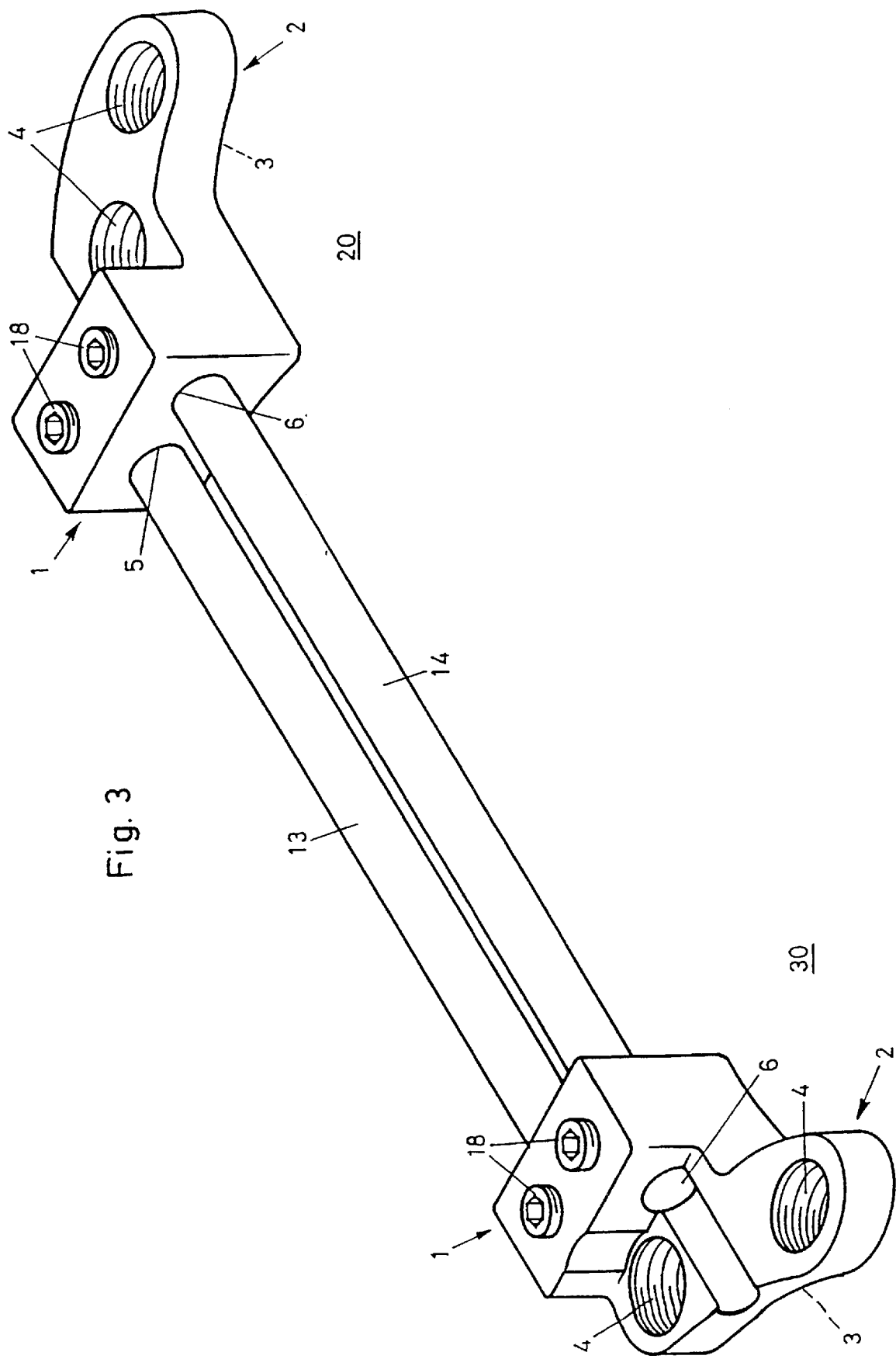
FIG. 3 a perspective representation of both devices according to the invention according to FIG. 1 and 2 which are mounted on two longitudinal carriers.

The device 20 for the fixation of bones according to the invention shown in FIG. 1 essentially consists of a block 1 and a bone plate 2 connected thereto with a bone-contact surface 3 and two plate holes 4 running through the bone plate 2 and having centres lying on a common connecting line 12 in order to accommodate a bone fixation means such as a bone screw. The block 1 provides a first guide channel 5 in order to accommodate a first longitudinal carrier 13 and a second guide channel 6 in order to accommodate a second longitudinal carrier 14. The two guide channels 5;6 run parallel to each other whereby the axes 7;8 of the two guide channels 5;6 lie in a plane parallel to the bone-contact surface 3. The circular cylinder 9 defined by the first guide channel 5 does not intersect the circular cylinders 10 defined each by the plate holes 4 whilst the circular cylinder 11 defined by the second guide channel 6 intersects one of the circular cylinders 10 defined each by the plate holes 4 (FIG. 1 and 3).

The first guide channel 5 completely penetrates the block 1 so that a longitudinal carrier 13 inserted therein can be pushed in any arbitrary axial position. Whereas the second guide channel 6 is formed as a pocket hole which opens at the side opposite to the bone plate 2. A longitudinal carrier 14 can consequently only be pushed until the maximum depth of the pocket hole and can not reach into the area of the circular cylinders 10 defined by the plate holes 4. The two guide channels 5;6 provide two bore holes 17 running perpendicularly to their axes 7;8 in order to accommodate fixation means 18 (in the form of adjustment screws) for the longitudinal carriers 13;14.

The connecting line 12 which connects the two plate holes 4 encloses a positive angle of +30° with the axes 7;8 of the two guide channels 5;6. This angle may vary in the range between +10° and +50° preferably between +20° and +40°.

The bone-contact surface 3 forms a cylinder segment having a cylinder radius of 30 mm whereby the axis of the cylinder segment runs parallel to the longitudinal axes 7;8 of the guide channels 5;6. The cylinder radius may vary within a range between 25 and 35 mm preferably between 29–31 mm.

The longitudinal axes of the plate holes 4 lie in parallel planes that are perpendicular to the longitudinal axis of the bone-contact surface 3 shaped as a cylinder segment.

Figure 2:
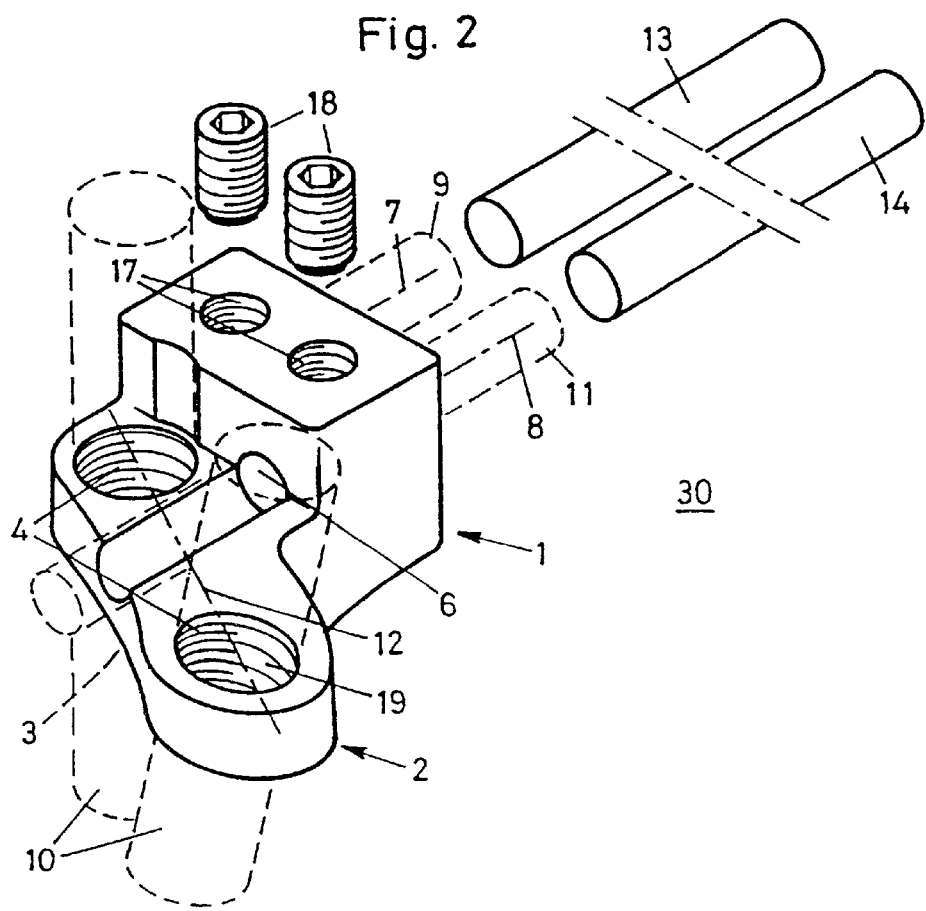
FIG. 2 a perspective representation of a second device according to the invention which is complementary to the first device.

In FIG. 2 a device 30 that is complementary to the device 20 is represented which differs particularly therein that the connecting line 12 encloses a negative angle of −30° with the axes 7;8 of the guide channels 5;6. This angle may vary in the range between −10° and −50° preferably between −20° and −40°.

As shown in FIG. 3 the two devices 20 and 30 can be combined to a combined device with the longitudinal carriers 13;14, whereby a first longitudinal carrier 13 is insertable into the first guide channel 5 of the one device 20 and into the second guide channel 6 of the other device 30 and a second longitudinal carrier 14 is insertable into the second guide channel 6 of the one device 20 and into the first guide channel 5 of the other device 30.

The distance between the two devices 20;30 to one another is adjustable through displacement on the two longitudinal carriers 13;14 and can be fastened in any arbitrary position by means of the fixation means 18 in the form of adjustment screws.

Figure 4:
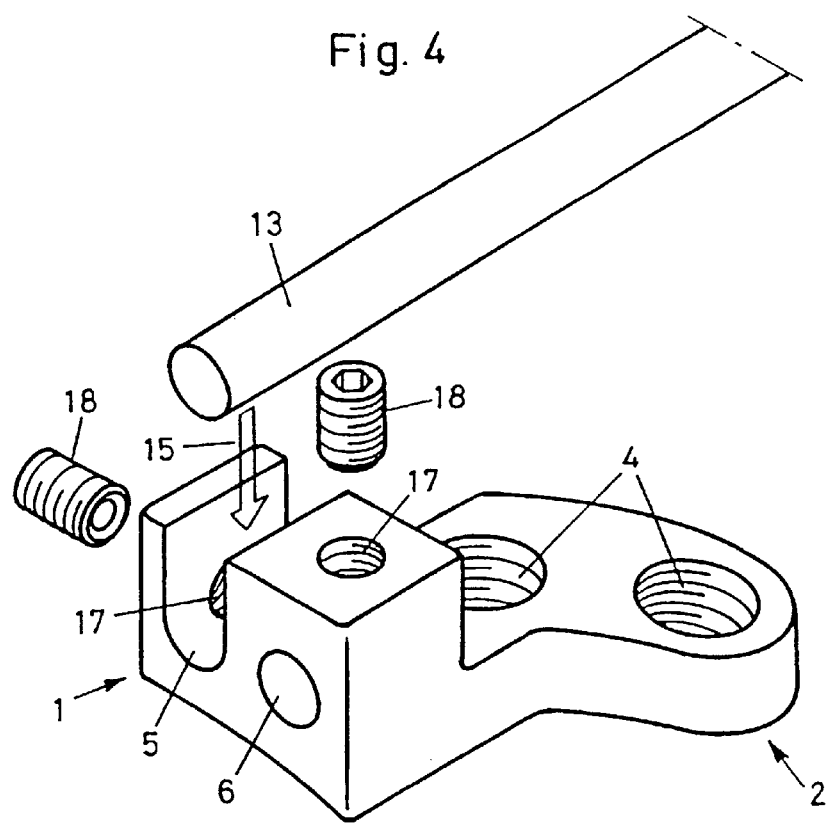
FIG. 4 a perspective representation of a first modification of a device according to the invention with a longitudinal carrier that is not yet inserted.

As shown in FIG. 4 the device 20 can be modified such that the first guide channel 5 is shaped open on the side opposite to the bone-contact surface 3 so that a longitudinal carrier 13 is insertable from above—in the direction of the arrow 15.

Figure 5:
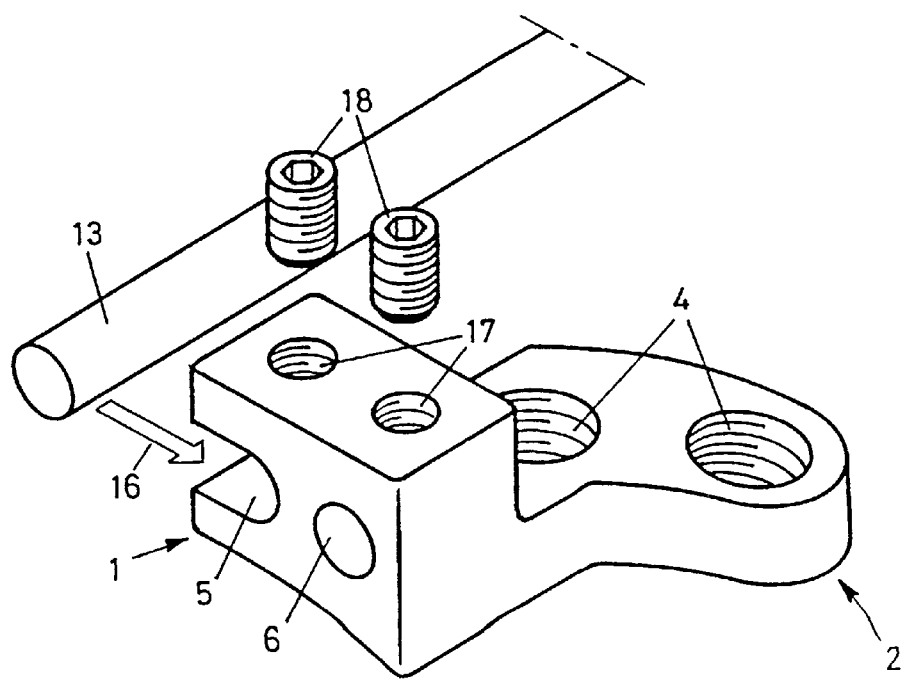
FIG. 5 a perspective representation of a second modification of a device according to the invention with a longitudinal carrier that is not yet inserted.

A further embodiment of the device 20 is shown in FIG. 5 and consists therein that the first guide channel 5 is shaped open in the direction of its adjacent side surface 24 of the block 1 so that a longitudinal carrier 13 is insertable from the side—in the direction of the arrow 16.

Figure 6:
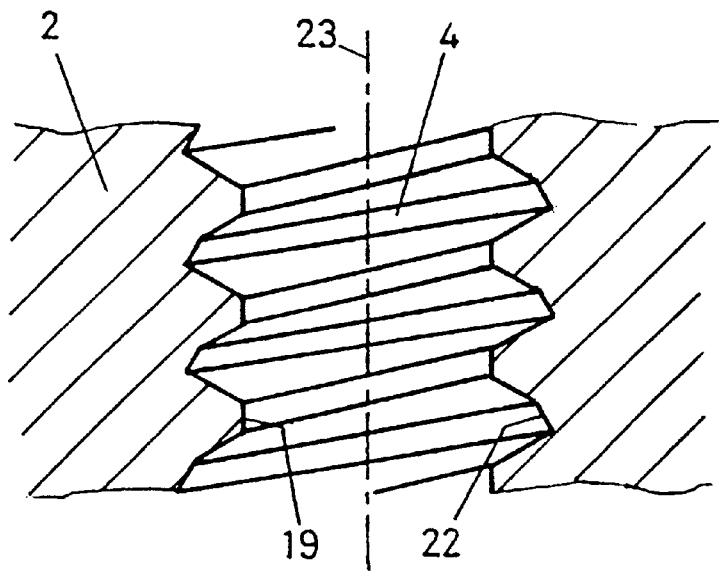
FIG. 6 a longitudinal cut through a plate hole with thread.

As shown in FIG. 6 the plate holes 4 can provide a multiple-threaded thread 19 which can accommodate a respective shaped bone screw—providing a external thread in the head area—so that a rigid and axially aligned connection between bone screw and bone plate 2 results. The thread 19 provides a planar thread bottom 22 which forms an angle of 30° together with the longitudinal axis 23 of the thread. The angle may vary in a range between 20° and 40° preferably between 29°–31°.

Figure 7:
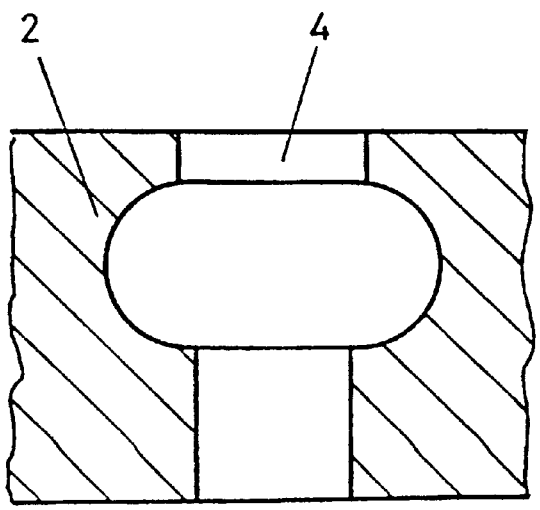
FIG. 7 a longitudinal cut through a plate hole shaped spherical.

The plate holes 4 can also be shaped spherical as shown in FIG. 7 in order to accommodate a slotted sphere with a conical bore hole for the bone screw so that the bone screw can be adjusted under a defined angle to the bone plate 2 and can be fastened angular stable.

In the following the course of the surgical application of the device according to the invention is described in more detail.

For or after the treatment of the anterior lesion the respective vertebral bodies are spread by means of a vertebral spreader and bone splinters respectively vertebral replacement bodies are inserted into the produced defect. Afterwards the length of the longitudinal carriers to be used is defined. Into each of the second guide channels 6 which are shaped as pocket holes of each device 20;30 according to the invention a longitudinal carrier 13;14 is inserted and fastened by means of an adjustment screw 18.

The devices 20;30 each instrumented with a longitudinal carrier 13 respectively 14 are assembled as shown in FIG. 3 to a combined device. This happens that way that the free ends of the longitudinal carriers 13;14 are pushed in the first guide channel 5 of the respectively other device 20 respectively 30 according to the invention and slightly fastened with an adjustment screw 18.

Each of both—now connected to each other—devices 20;30 according to the invention is now instrumented with an implant holder (not shown in the drawings) e.g. a sleeve of a drill jig with an integrated awl in the plate holes 4. The combined device is now pressed with the implant holders sidewardly against the vertebral column, the first bore awl is released, a bore hole is drilled, the sleeve of a drill jig with the integrated bore awl taken away and a bone screw turned into the bore hole drilled into the bone through the plate hole 4. Afterwards the second bore awl is released, a bore hole drilled, the sleeve of a drill jig with the integrated bore awl taken away and a bone screw turned into the drilled bore hole.

As long as only one bone screw each is turned into the particular vertebral bodies it may still be kyphosised or lordosised.

Now the sleeves of a drill jig with integrated awl are turned into the resting plate holes 4 and processed as described above.

The zone fusioned by means of the combined device may now be compressed so that the adjustment screws 18 which fasten the two longitudinal carriers 13;14 in the first guide channels 5 are loosened and the blocks 1 of the both devices 20;30 according to the invention are pushed together by means of a compression nippers.

What is claimed is:

1. A device for fixing bones comprising:
   a block having a top, bottom and sides;
   a bone plate associated with the block and having a bone-contact surface and first and second plate holes passing therethrough, each hole configured and dimensioned for accommodating a fastener; and
   first and second parallel guide channels associated with the block for accommodating first and second longitudinal carriers, and each having a longitudinal axis lying in a plane which is parallel to the bone-contact surface;
   wherein an imaginary cylinder defined by the first guide channel does not intersect an imaginary cylinder defined by the first bone plate hole, and an imaginary cylinder defined by the second guide channel intersects an imaginary cylinder defined by the second bone plate hole.

2. The device according to claim 1 wherein the first guide channel extends completely through the block.

3. The device according to claim 1 wherein the second guide channel extends partially through the block to form an opening in the block opposite the bone plate.

4. The device according to claim 1 wherein first and second plate holes have centers which lie on a common connecting line.

5. The device according to claim 1 wherein at least one of the guide channels extends to the side of the block opposite the bone-contact surface to facilitate insertion of a longitudinal carrier.

6. The device according to claim 1 wherein at least one of the guide channels extends to the top of the block to facilitate insertion of a longitudinal carrier.

7. The device according to claim 1 wherein each guide channel includes a bore hole positioned orthogonal to its longitudinal axis to accommodate a fastener for removably securing a longitudinal carrier to the guide channel.

8. The device according to claim 4 wherein the connecting line is disposed at an angle of +10° to +50° with respect to the longitudinal axes of the first and second guide channels.

9. The device according to claim 4 wherein the connecting line is disposed at an angle of −10° to −50° with respect to the longitudinal axes of the first and second guide channels.

10. The device according to claim 1 wherein the bone-contact surface includes a cylindrical segment having a cylinder radius of between 25 and 35 mm and a longitudinal axis which is parallel to the longitudinal axes of the first and second guide channels.

11. The device according to claim 10 wherein the plate holes have longitudinal axes lying in parallel planes which are perpendicular to the longitudinal axis of the cylindrical segment of the bone-contact surface.

12. The device according to claim 1 wherein at least one of the first and second plate holes has a multiple-threaded thread.

13. The device according to claim 12 wherein the thread has a planar thread bottom.

14. The device according to claim 13 wherein the planar thread bottom forms an angle of between 20° and 40° with respect to the thread longitudinal axis.

15. The device according to claim 1 wherein at least one of the first and second plate holes is spherical.

16. An apparatus for fixing bones comprising:
    first and second devices each comprising:
      a block having a top, bottom and sides;
      a bone plate associated with the block and having a bone-contact surface and first and second plate holes passing therethrough, each hole configured and dimensioned for accommodating a fastener; and
      first and second parallel guide channels associated with the block for accommodating first and second longitudinal carriers, and each having a longitudinal axis lying in a plane which is parallel to the bone-contact surface;
      wherein an imaginary cylinder defined by the first guide channel does not intersect an imaginary cylinder defined by the first bone plate hole, and an imaginary cylinder defined by the second guide channel intersects an imaginary cylinder defined by the second bone plate hole; and
    first and second longitudinal carriers positioned in the first and second guide channels of the first and second devices.

17. The apparatus according to claim 16 wherein each guide channel includes a bore hole positioned orthogonal to its longitudinal axis to accommodate a fastener for removably securing the longitudinal carrier therein.

18. The apparatus according to claim 16 wherein the first and second plate holes of each bone plate have centers which lie on a common connecting line.

19. The apparatus according to claim 18 wherein at least one guide channel of each of the first and second devices extends to the side of the block opposite the bone-contact surface to facilitate insertion of the longitudinal carrier.

20. The apparatus according to claim 18 wherein at least one guide channel of each of the first and second devices extends to the top of the block to facilitate insertion of the longitudinal carrier.

* * * * *